(12) United States Patent
Brevnov et al.

(10) Patent No.: US 9,422,544 B2
(45) Date of Patent: Aug. 23, 2016

(54) METHODS AND KITS FOR EXTRACTION OF DNA

(71) Applicant: Life Technologies Corporation, Carlsbad, CA (US)

(72) Inventors: Maxim Brevnov, Union City, CA (US); Hemant Pawar, Ann Arbor, MI (US); Manohar Furtado, San Ramon, CA (US); Jaiprakash Shewale, Santa Clara, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 34 days.

(21) Appl. No.: 13/931,110

(22) Filed: Jun. 28, 2013

(65) Prior Publication Data
US 2014/0039176 A1    Feb. 6, 2014

Related U.S. Application Data

(63) Continuation of application No. 12/371,515, filed on Feb. 13, 2009, now Pat. No. 8,497,065.

(60) Provisional application No. 61/028,986, filed on Feb. 15, 2008.

(51) Int. Cl.
| | | |
|---|---|---|
| C07H 21/02 | (2006.01) | |
| C12Q 1/68 | (2006.01) | |
| C12N 15/10 | (2006.01) | |

(52) U.S. Cl.
CPC ........ *C12N 15/1013* (2013.01); *C12N 15/1006* (2013.01); *C12Q 1/6806* (2013.01)

(58) Field of Classification Search
CPC ........... C12Q 1/6806; C12Q 2523/308; C12Q 2563/143; C12N 15/1006; C12N 15/1013
See application file for complete search history.

(56) References Cited

U.S. PATENT DOCUMENTS

| | | |
|---|---|---|
| 5,523,231 A | 6/1996 | Reeve |
| 5,614,652 A | 3/1997 | Filler et al. |

(Continued)

FOREIGN PATENT DOCUMENTS

| | | |
|---|---|---|
| CN | 1535979 | 10/2004 |
| WO | 91/12079 | 8/1991 |

(Continued)

OTHER PUBLICATIONS

Brevnov, M. et al., "Developmental Validation of the PrepFiler (TM) Forensic DNA Extraction kit for extraction of Genomic DNA from Biological Samples", Journal of Forensic Sciences, vol. 54 (3), May 2009, 599-607.

(Continued)

*Primary Examiner* — Teresa E Strzelecka (57) ABSTRACT

Methods and materials are disclosed for use in recovering a biopolymer from a solution. In particular, the invention provides methods for extraction and isolation of nucleic acids from biological materials. The nucleic acids can be separated by forming a stable complex with soluble polysaccharide polymers and magnetic particles, in the presence of detergents and solvent. When the particles are magnetically separated out of the solution, the nucleic acids are separated with them. The nucleic acids can subsequently be released and separated from the particles. The nucleic acid preparation is useful for achieving efficient and accurate results in downstream molecular techniques such as quantification, identification of the source of the nucleic acids, and genotyping.

5 Claims, 4 Drawing Sheets

(56) References Cited

U.S. PATENT DOCUMENTS

| | | |
|---|---|---|
| 5,681,946 A | 10/1997 | Reeve |
| 7,169,618 B2 | 1/2007 | Skold |
| 2004/0137449 A1 | 7/2004 | Nargessi |
| 2005/0042656 A1 | 2/2005 | Davis et al. |
| 2005/0208510 A1 | 9/2005 | Latham et al. |
| 2006/0003357 A1 | 1/2006 | McKernan et al. |
| 2006/0078923 A1 | 4/2006 | McKernan et al. |
| 2006/0177855 A1 | 8/2006 | Utermohlen et al. |
| 2009/0209751 A1 | 8/2009 | Brevnov et al. |
| 2010/0029925 A1 | 2/2010 | Brevnov et al. |

FOREIGN PATENT DOCUMENTS

| | | |
|---|---|---|
| WO | 96/18731 | 6/1996 |
| WO | 97/08547 | 3/1997 |
| WO | 2005/089929 | 9/2005 |
| WO | 2009/103018 A2 | 8/2009 |
| WO | 2009/103018 A3 | 8/2009 |
| WO | 2009/143499 | 11/2009 |

OTHER PUBLICATIONS

Kishore, Ram et al, "Journal of Forensic Sciences", *"Optimization of DNA extraction from low yield and degraded samples using the BioRobot (R) EZI and BioRobot (R) M48"*, 2006, 1055-1061.

PCT/US2009/034143, , "International Preliminary Report on Patentability", Mailed Aug. 26, 2010, 7 pages.

PCT/US2009/034143, , "International Search Report", Mailed Sep. 14, 2009, 13 Pages.

PCT/US2009/045092, , "International Preliminary Report on Patentability", Mailed Dec. 2, 2010, 6 pages.

PCT/US2009/045092, , "International Search Report", Mailed Jul. 29, 2009, 11 pages.

METHODS AND KITS FOR EXTRACTION OF DNA

INTRODUCTION

The present teachings are generally directed to methods of isolating nucleic acids from biological materials, such that the nucleic acids are compatible with use in downstream applications. In various embodiments, the present teachings relate to the use of polyhydroxy polymers and detergents for binding of nucleic acids to, and release of nucleic acids from, magnetic particles with hydrophilic surfaces. In some embodiments, kits are provided for isolating DNA from biological materials.

The section headings used herein are for organizational purposes only and are not to be construed as limiting the subject matter described in any way. All literature and similar materials cited in this application, including but not limited to patents, patent applications, articles, books and treatises, regardless of the format of such literature and similar materials, are expressly incorporated by reference in their entirety for any purpose.

DRAWINGS

The skilled artisan will understand that the drawings, described below, are for illustration purposes only. The drawings are not intended to limit the scope of the present teachings in any way.

FIG. 4(A-E) demonstrates genotyping profiles obtained following DNA isolation and purification from substrates as described in Example 13, wherein genomic DNA was isolated from biological samples according to the methods of Example 11, and was processed for genotyping using the Identifiler® kit.

DESCRIPTION OF VARIOUS EMBODIMENTS

While the present teachings are described in conjunction with various embodiments, it is not intended that the present teachings be limited to such embodiments. On the contrary, the present teachings encompass various alternatives, modifications and equivalents, as will be appreciated by those of skill in the art.

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control. Headings used herein are merely for convenience, and are not to be construed as limiting in any way.

As used herein, "DNA" refers to deoxyribonucleic acid in its various forms as understood in the art, such as genomic DNA, cDNA, isolated nucleic acid molecules, vector DNA, and chromosomal DNA. "Nucleic acid" refers to the nucleic acid molecule or molecules, DNA or RNA (ribonucleic acid) in any form. As used herein, the term "isolated nucleic acid molecule" or "isolated nucleic acid" refers to a nucleic acid molecule (DNA or RNA of any form) that has been removed from its native environment. Some examples of isolated nucleic acid molecules are recombinant DNA molecules contained in a vector, recombinant DNA molecules maintained in a heterologous host cell, partially or substantially purified nucleic acid molecules, nucleic acids obtained from forensic and other samples comprising biological material, such as blood, semen, saliva, skin tissue, etc., and synthetic DNA molecules. An "isolated" nucleic acid can be free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

"Polymerase chain reaction" (or "PCR") refers to a technique in which repetitive cycles of denaturation, annealing with a primer, and extension with a DNA polymerase enzyme are used to amplify the number of copies of a target DNA sequence by approximately $10^6$ times or more. The PCR process for amplifying nucleic acids is covered by U.S. Pat. Nos. 4,683,195 and 4,683,202, which are herein incorporated in their entirety by reference for a description of the process. The reaction conditions for any PCR comprise the chemical components of the reaction and their concentrations, the temperatures used in the reaction cycles, the number of cycles of the reaction, and the durations of the stages of the reaction cycles.

"PCR-compatible" refers to any composition, solution, compound, reagent, etc. that is compatible with subsequent use in PCR assays and is relatively non-inhibitory of the enzymatic polymerase chain reaction. PCR-compatible products demonstrate relatively minimal or no inhibition of PCR amplification, as evidenced by comparison of PCR results with the relevant positive and negative controls. PCR assays can include, but are not limited to, DNA genotyping systems, TaqMan® or SYBR® green real-time PCR assays for DNA quantification, multiplex PCR assays including those designed to genotype short tandem repeats, etc.

As used herein, "amplify" refers to the process of enzymatically increasing the amount of a specific nucleotide sequence. This amplification is not limited to but is generally accomplished by PCR.

"Polymer" or "polymers" refer to soluble polyhydroxy polymers for binding of nucleic acids to, and release of nucleic acids from, magnetic particles with hydrophilic surfaces.

In some embodiments of the present teachings, methods are described in which nucleic acid molecules can be separated and/or isolated from samples and, in some embodiments, in which the product made from the methods are nucleic acids. In some embodiments, the methods of the present teachings result in the formation of a product which comprises the isolated nucleic acid.

In some embodiments of the present teachings, nucleic acid molecules can be separated and/or isolated from samples containing biological materials and, in some embodiments, the product made from the methods are nucleic acids. Examples of such samples include but are not limited to blood and blood stains, saliva and saliva stains, buccal cells and buccal swabs, semen and semen stains, cigarette butts, and chewing gum.

In some embodiments of the present teachings, methods are described wherein a sample can be treated with a starting solution comprising soluble polyhydroxy polymers and detergent, and adding magnetically attractable particles in order to recover nucleic acid molecules from the sample and, in some embodiments, nucleic acids are recovered from the sample by applying a magnetic field. In various embodiments, the sample can comprise one or more of free nucleic acids; cells; biological materials such as buccal swabs, stained fabrics, and so on. In additional embodiments of the present teachings, methods are described wherein a nucleic acid can be separated from a sample, comprising the steps of treating the sample with a starting solution comprising a polymer and detergent; adding suspended magnetically attractable particles to the treated sample; and separating the nucleic acid attached to the magnetically attractable particles via the polymer by applying a magnetic field. Such methods may further comprise the step of releasing the nucleic acid from the magnetically attractable particles. Such methods may yet further comprise the step of eluting the nucleic acid in an aqueous solution.

The nucleic acids thus obtained can then be utilized in any of various downstream applications such as, for example, quantification, detection, and genotyping of specific nucleic acids or even of a biological species. These analyses can be performed, for example, by PCR amplification. As one example, in forensic DNA analysis the human nuclear DNA (nDNA) and/or genomic DNA can be obtained from complex biomaterials and then genotyped using PCR. As another example, a DNA preparation can be used for quantification of human DNA, or more specifically human male DNA, using real-time PCR systems such as Quantifiler®, and/or genotyped for autosomal or Y-chromosomal short tandem repeat loci using systems such as, for example, AmpFISTR® kits. Based upon the amount of DNA present in a sample, a particular genotyping system can be selected that will yield the best results for the particular analysis required. Therefore, in order to best utilize nucleic acids in downstream applications, it is particularly desirable that the methods result not only in a product of high yield, but also one that is relatively free of inhibitors of downstream applications such as PCR.

As an example, typical forensic evidence samples are often exposed to various environmental insults during acquisition and processing, which can lead to contamination with compounds that act to inhibit PCR, and which therefore interfere with attempts at genotyping or other analyses. It is desirable to remove such inhibitors during the isolation of DNA and prior to amplification.

Various embodiments of the present teachings relate to efficient binding of nucleic acids such as, for example, genomic DNA to magnetic particles (i.e., magnetically attractable particles, or beads) in such a form that the bound nucleic acids can then be released under the appropriate aqueous conditions. Embodiments of these teachings thus enable effective isolation of nucleic acids, such as genomic DNA, from various different types of biological materials. In addition, nucleic acids such as genomic DNA can be isolated from either small or large quantities of the biological materials that are commonly processed in laboratories such as, for example, those involved in genotyping analyses.

These embodiments and other features of the present teachings will become more apparent from the description herein.

Nucleic Acid Isolation System

Various embodiments of the present teachings relate to a system, amenable to assembly in a kit, for the binding of nucleic acids such as genomic DNA to magnetic particles having a hydrophilic surface via soluble polyhydroxy polymers, in the presence of detergents, forming a nucleic acid-polymer-particle complex, and the production and isolation of such a complex, wherein the nucleic acid does not directly bind to the magnetic particles. The formation of the complex is such that the polymer entraps the nucleic acid, polymer attaches to the particles, and so indirectly connects the nucleic acid with the particles. Various embodiments comprise a lysis solution, which causes the lysis of cells and release of nucleic acid, while protecting the nucleic acid from degradation and removing PCR inhibitors. In various embodiments of the present teachings the nucleic acids remain bound to the magnetic particles via the complex in the presence of a wash solution, in which the complex is washed so as to remove contaminants and so that the nucleic acid is amendable to use in downstream applications, such as PCR. Solutions for washing nucleic acid isolations of any contaminants and inhibitors are well-known to those of skill in the art, and can comprise, for example, detergents and polar solvents. In embodiments of the present teachings, the nucleic acids can then be released in an aqueous solution, such as a buffer, which is also compatible for use in downstream applications such as PCR. A plurality of washes can be performed in the methods of the present invention, separately or in conjunction with a plurality of applications of the magnetic field to the sample to recover and/or separate the nucleic acids.

Standard nucleic acid extraction techniques, including cell lysis, and washing and elution of nucleic acids, are well known in the art and unless otherwise noted, can be carried out according to various techniques as described, for example, in *DNA Typing Protocols: Molecular Biology and Forensic Analysis,* $1^{st}$ edition, B. Budowle et al., eds., Eaton Publishing Co. (2000); J M Butler, *Forensic DNA Typing: Biology, Technology, and Genetics of STR Markers,* $2^{nd}$ edition, Elsevier Academic Press (2005); or P. Gill, "Application of Low Copy Number DNA Profiling," *Croatian Medical Journal* vol. 42, pages 229-232 (2001); F R Bieber et al., "Isolation of DNA from Forensic Evidence," *Current Protocols in Human Genetics,* Supplement 26 (2000); *Forensic DNA Profiling Protocols, Methods in Molecular Biology,* vol. 98, P J Lincoln and J. Thomson, eds., Humana Press (1998).

Various embodiments of the present teachings relate to a nucleic acid isolation system, such as for genomic DNA, comprising reagents and methods for extraction of the nucleic acids from biological samples. Embodiments of these methods can comprise: forming a non-covalent complex of nucleic acid (e.g., genomic DNA) with soluble polymers having the same or similar chemical structure as the surface of magnetically attractable particles, in the presence of detergents; binding of the nucleic acid-polymer complex to magnetic particles via interactions between the polymers and surfaces of the particles, thus forming a stable nucleic acid-polymer-particle complex; releasing the nucleic acid from the particles, and eluting the nucleic acid in an aqueous solution.

Applicants have found that the use of polyhydroxy water-soluble polymers and detergent, in the presence of appropriate salts and polar solvent, improves the efficiency of the binding and release of nucleic acids such as genomic DNA on the surface of magnetically attractable particles. An example of appropriate magnetically attractable particles is, but is not limited to, dextran-encased Nanomag® magnetite nanoparticles. In some embodiments of the present teachings, dextran-encased magnetite nanoparticles are added to a sample comprising nucleic acids in the range of about 2 to about 10 mg/ml.

The soluble polymers and detergent may be termed binding enhancers. Some examples of appropriate polyhydroxy water-soluble polymers are, but are not limited to, long-chain branched polysaccharides such as dextrans (e.g., dextran 5,000,000-40,000,000), soluble starch, dextrins, cellodextrins, polyethylene glycol (PEG), heparin, glycogen, short-chain cellulose, cellulose derivatives, and combinations thereof. Some examples of appropriate detergents are, but are not limited to, N-lauroyl sarcosine (NLS); lauroyl sarcosinate, also known as sarcosyl, an ionic surfactant derived from sarcosine; hexadecyltrimethylammonium bromide or cetyltrimethylammonium bromide (CTAB); deoxycholate; dodecyl β-D-maltoside; nonanoyl-N-methylglucamide; sodium dodecyl sulfate; polyethylene glycol p-(1,1,3,3-tetramethylbutyl)-phenyl ether (commercially known as Triton® X-100); and combinations thereof. In some embodiments, the binding enhancer comprises dextran in the range of 1-5 mg/ml and sarcosyl in the range of about 5 to about 15%.

Some examples of appropriate polar solvents are, but are not limited to, isopropanol, ethanol, butanol, and combinations thereof. In some embodiments, the polar solvent comprises about 80% to about 100% isopropanol.

In some embodiments, magnetically attractable particles can be added to a sample comprising nucleic acid, such as a cell lysate, at the same time as the binding enhancers, forming a suspension. A solution comprising polar solvent can then be added to this suspension. Alternatively, in some embodiments of the present teachings a single solution comprising binding enhancers and polar solvent can be added to the suspension. Binding enhancers, solvent and cell lysate provide unique conditions such that nucleic acids are entrapped in a non-covalent complex with soluble polymers having the same or a similar chemical structure as the surface of the magnetic particles. The result is the effective binding of the polymer-entrapped nucleic acids to the magnetic particles in a non-covalent nucleic acid-polymer-particle complex. This complex is stable under alcohol wash conditions, and the nucleic acids can easily be later eluted in a standard low-salt buffer such as, for example, Tris buffer containing low concentrations of divalent metal ion chelating agents, such as EDTA. In some embodiments, this stage of nucleic acid-polymer binding to particles may be assisted by chilling.

Following binding of the polymer-entrapped nucleic acids to magnetic particles in the formation of the nucleic acid-polymer-particle complexes, a magnetic field can then be applied to the suspension. This magnetic field can be used to remove the nucleic acid-polymer-particle complexes from the suspension, forming a complex layer, for example, at the bottom or side of the tube and leaving a supernatant. The magnetic field can be applied to the sample by devices and methods known in the art (e.g., via Ambion® (Austin, Tex.) Magnetic Stands). The supernatant can then be removed from the tube.

The nucleic acid-polymer-particle complex layer can then optionally be washed, to remove residual contaminants and/or inhibitors of PCR; then the nucleic-acid-polymer-particle complex can be resuspended in the requisite volume of an appropriate elution buffer in the absence of any magnetic field. The appropriate elution buffers for the isolation of nucleic acids are well-known to those of skill in the art. These allow for release of the nucleic acids into solution from the nucleic acid-polymer-particle complexes. A magnetic field can be reapplied to the tube, resulting in removal of the magnetic particles from the suspension to, for example, the bottom or side of the tube, leaving a supernatant in which the nucleic acid is now dissolved. The redissolved nucleic acid can now be separated from the magnetic particles by collecting the supernatant with, for example, a pipette while the particles are held against the bottom or side of the tube by the magnetic field. Centrifugation of the sample is not required in these methods.

Figure 1:
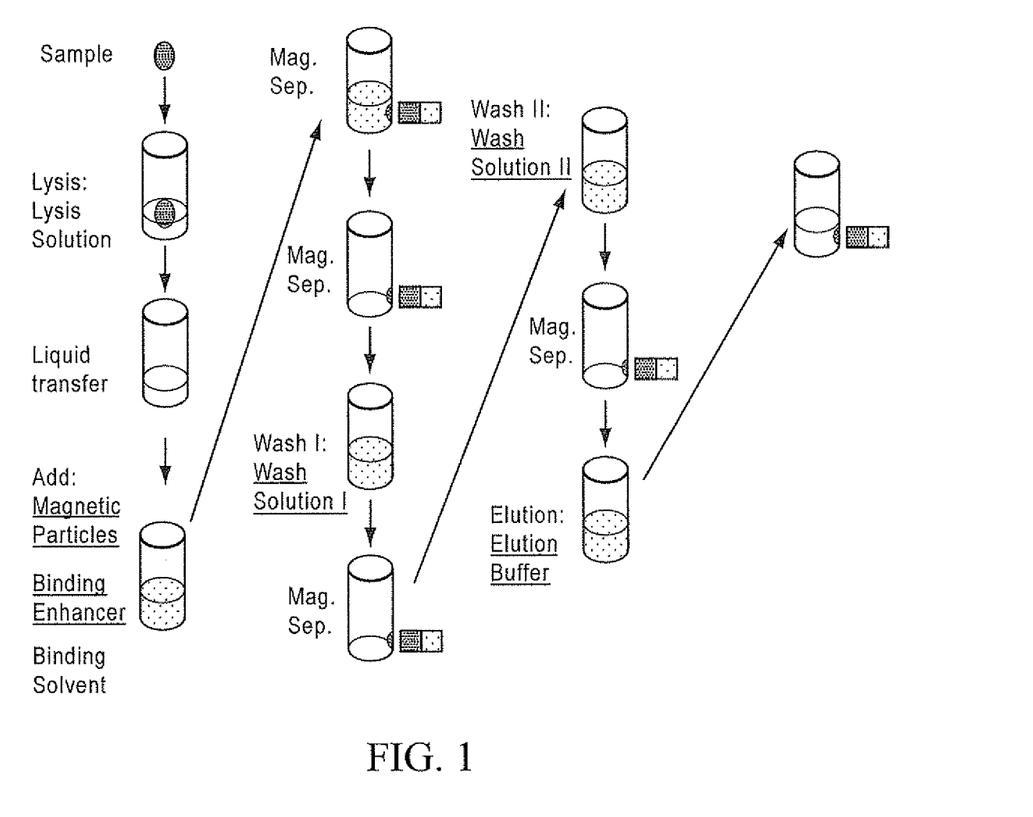
FIG. 1 is a schematic demonstrating a method of DNA isolation and purification, as described in various embodiments of the present teachings.

In some embodiments of the present teachings, then, nucleic acid molecules can be isolated from samples containing biological materials and purified from solution in combination with the use of magnetic particles with a hydrophilic surface, such as, for example, magnetic dextran particles. Magnetic particle-facilitated nucleic acid isolation and purification can be used to greatly improve upon the traditional process of alcohol-based precipitation isolation and purification of nucleic acids, well-known to those of skill in the art. An example of an embodiment of an alcohol-based isolation and purification procedure as modified by these teachings can be demonstrated by reference to FIG. 1.

Lysis Solution

Embodiments of the methods described herein can comprise the lysing of cells from biological materials present on a substrate such as, for example, the cotton of a buccal swab or a stained fabric, to create a lysate comprising nucleic acids; removing the substrate from the lysate; forming the nucleic acid-polymer-particle complex, followed by separating and eluting of nucleic acids as described above. In one embodiment, the lysis solution can comprise SDS, Tris buffer and NaCl, optionally with proteinase K; and in some embodiments the lysis solution can comprise 0.0%-1% SDS, 100 mM Tris buffer, and 2 M NaCl.

In various embodiments of the present teachings, a lysis solution can be added to a sample containing biological material (and optionally, the sample subjected to heat for some time, e.g., twenty minutes to two hours) in order to lyse cells and free nucleic acids into a lysate. In some embodiments the lysis solution can be a composition comprising compounds designed to effectively lyse cells, e.g., buccal cells collected on a cotton swab, while also protecting released nucleic acids from degradation. In some embodiments the lysis solution further comprises such compounds as to ensure that released nucleic acids are compatible with use in downstream assays such as, for example, PCR assays, and in particular DNA genotyping systems.

In some embodiments of the present teachings, magnetic particles, binding enhancers and polar solvent can then be added to the lysate comprising the nucleic acid following the lysis procedure, creating a suspension in which the nucleic acid-polymer-particle complexes are formed, and the nucleic acids are separated and eluted as describe above.

Wash Solution

Various embodiments of the present teachings relate to a nucleic acid isolation system, such as for genomic DNA, comprising reagents and methods for extraction of the nucleic acids from a biological sample, and comprise a wash step to remove PCR inhibitors from the sample. The wash solution used in the wash step is such as are known in the art. In some embodiments, a particular component of the wash solution can be ethanol in a concentration ranging from 70%-90%. Embodiments of these methods can comprise: formation of a non-covalent complex of nucleic acid (e.g., genomic DNA) with soluble polymers having the same or similar chemical structure as the surface of magnetic particles; binding of the nucleic acid-polymer complex to magnetic particles via interactions between the polymers and surfaces of the particles, thus forming a stable nucleic acid-polymer-particle complex; removal of unbound materials, such as PCR inhibitors, via a wash solution reagent comprising detergent and polar solvent; and elution of the nucleic acid in an aqueous solution amenable to use in downstream applications such as PCR.

Using a wash solution of detergents and polar solvent to wash the nucleic acid-polymer-particle complex helps remove any residual salt, nucleotides, chemicals, organic solvents, and other contaminants in the sample, and improves the removal of inhibitors of downstream applications, such as PCR inhibitors. In various embodiments, a wash solution can be used as a wash of nucleic acid-polymer-particle complexes to remove PCR inhibitors and/or contaminants. Solutions useful for washing nucleic acids during isolation and/or purification are well-known to those of skill in the art.

In some embodiments, a wash solution is added to the nucleic acid-polymer-particle complex to create a wash suspension. The nucleic acid is insoluble in alcohol, and remains in a stable complex with the polymers and particles during washing. The washing step can thus be performed vigorously (e.g., by vortex mixing) without risk of loss of the nucleic acids. The sample can then be placed before a magnetic field again, and the resultant wash supernatant comprising contaminants can be removed from the complex layer, which separates out of the wash suspension.

After the washing step, if performed, a second wash step can also be performed following similar steps as in the first wash. In some embodiments of the present teachings, following the wash step(s) the nucleic acids are separated and eluted as describe above.

Nucleic Acid Extraction and Purification

The extraction and purification methods of the present teachings provide useful methods for obtaining nucleic acids such as genomic DNA from biological samples which can be used in downstream applications such as genotyping, quantification, and identification of the source of the biological material, wherein molecular biological processes such as PCR are utilized. The exemplary results described in the Examples herein illustrate the various advantages of the nucleic acid extraction and purification methods of the present teachings, which include but are not limited to providing a nucleic acid (e.g., genomic DNA) preparation that (a) can be derived from a variety of biological materials, (b) is free of detectable inhibitors of downstream applications, such as PCR amplification; (c) can be in concentrated form, and, (d) is amenable for use in any of various applications for nucleic acid analysis, such as genotyping, quantification, detection of the source of biological material, etc. Furthermore, the procedure for extraction and purification of nucleic acids is fully automatable, using standard liquid handling systems.

Additionally, modification of standard alcohol precipitation procedures currently in use, such as those requiring centrifugation, by the methods of the present teachings can provide several clear benefits. First, the methods herein exemplified by the present teachings are faster—the modified procedure for removal of solution from the separated nucleic acid complex takes only about 1-2 minutes, as opposed to about 10-30 minutes for conventional methods using centrifugation. Second, the methods are not reliant upon centrifugation equipment, but can be performed with a simple magnet setup. Third, the methods are more readily suited to automation. For example, a great many tubes could be placed over a large electromagnet and nucleic acids from these could all be isolated simultaneously using, e.g., a multi-channel pipetting device. Fourth, the methods of present teachings are especially effective for step of washing the nucleic acid-polymer-magnetic particle complexes (e.g., in order to remove any residual salt, nucleotides or organic solvents such as phenol), because in the present teachings the washing steps do not require centrifugation and so can be performed rapidly. Additionally, there is minimal or no risk of loss of material, as can occur with the conventional methods based upon centrifugation, where the pellet often detaches from the bottom of the tube during such washing.

As those skilled in the art will appreciate, numerous changes and modifications may be made to the various embodiments of the present teachings without departing from the spirit of these teachings. It is intended that all such variations fall within the scope of these teachings.

All of the compositions and methods of the present teachings, as disclosed and claimed herein, can be made and executed without undue experimentation in light of the present disclosure. While the compositions and methods of these teachings have been described in terms of specific embodiments, it will be apparent to those of skill in the art that variations may be applied to the compositions and methods, and in the steps or in the sequence of steps of the methods described herein, without departing from the concept and scope of these teachings. More specifically, it will be apparent that certain agents which are both chemically and physiologically related may be substituted for the agents described herein, while the same or similar results would be achieved. All such similar substitutes and modifications apparent to those skilled in the art are deemed to be within the scope of the invention as defined by the appended claims.

EXAMPLES

Aspects of the present teachings may be further understood in light of the following examples, which should not be construed as limiting the scope of the present teachings in any way.

Example 1

Samples of human body fluids were obtained in polypropylene tubes of 2.0 ml capacity. The samples were 2 µl blood, 10 µl saliva, and 2 µl semen. Each was mixed with a lysis solution in order to lyse cells. The lysis solution comprised 0.0%-1% SDS, 100 mM Tris buffer, and 2 M NaCl, optionally with proteinase K. The lysis mixtures were incubated with or without shaking at a temperature in the range of approximately 60° to 80° C. for a period of 40 minutes to 1 hour.

The genomic DNA released from the biological materials was then bound to the magnetic particles having the polyhydroxy groups of dextran. The binding mixture of each sample contained the cell lysate, 10 to 20 µl of a suspension comprising the magnetic particles at a concentration of approximately 5-20 mg/ml, and 150 to 300 µl of a polar compound such isopropanol, ethanol, and/or PEG. The DNA bound to the magnetic particles was then physically separated from the binding mixture by the application of a magnetic field to the mixture.

The DNA, still bound to the magnetic particles in a complex, was then washed with an alcohol-based wash solution (90% Ethanol). The DNA-magnetic particle complexes were again physically separated from the wash mixture by use of a magnetic field. The wash step was repeated one to two times. PCR inhibitors and other macromolecules entrapped in the DNA-magnetic particle complexes were removed in this wash step. The DNA was then released from the magnetic particles by suspending the DNA-particle complexes in 10 to 100 μl of aqueous solution, such as DNA-free water or a neutral buffer such as Tris-HCl, and this DNA release mixture was incubated at a temperature in the range of approximately 50 to 75° C. Released genomic DNA was then physically separated from the magnetic particles by use of a magnetic field. The genomic DNA preparation thus obtained was stored at 4° C. for short-term storage, or at −20° C. for long-term storage. The DNA was quantified by the use of standard methods well-known to those of skill in the art. The results thus obtained, typical for human genomic DNA, are presented in Table 1.

TABLE 1

| Sample | Yield of DNA, ng |
| --- | --- |
| 2 μl liquid blood | 8 |
| 2 μl liquid semen | 250 |
| 10 μl liquid saliva | 100 |

Example 2

Genomic DNA from biological samples was extracted and isolated as described in Example 1, wherein the binding mixture comprised: the cell lysate; 10 to 20 μl of the magnetic particle suspension wherein the particles possessed the polyhydroxy groups of dextrans; 10 to 20 μl of polyhydroxy polysaccharides such as dextran, cellulose, or soluble starch, at concentrations ranging from approximately 1 to 10 mg/ml; 10 to 20 μl of anionic detergents, such as N-lauroyl sarcosine, sodium deoxycholate, CTAB, N-dodecyl β-D-maltoside, nonanoyl-N-methylglucamide, Triton® X-100 or sodium dodecyl sulfate; and 150 to 300 μl of a polar compound such as isopropanol, ethanol, and/or PEG. The yield of genomic DNA obtained from this method is presented in Table 2.

TABLE 2

| Sample | Yield of DNA, ng |
| --- | --- |
| 2 μl liquid blood | 140 |
| 2 μl liquid semen | 1200 |
| 10 μl liquid saliva | 200 |

Example 3

Genomic DNA from biological samples was extracted and isolated as described in Example 2, wherein the inhibitors and other macromolecules entrapped in the DNA bound to the magnetic particles were removed using two different wash solutions. The step of washing the DNA bound to the magnetic particles comprised one wash with the first wash solution, then one to two wash steps using the second wash solution.

Example 4

Samples of the human body fluids 2 μl of blood, 20 μl of saliva, and 1 μl of semen were obtained in a polypropylene tube of 2.0 ml capacity and mixed with a lysis solution. The lysis mixture was incubated with or without shaking at a temperature in the range of approximately 60 to 80° C. for a period of approximately 40 minutes to 4 hours.

The genomic DNA released from the biological materials was then bound to the magnetic particles comprising the polyhydroxy groups of dextran. The binding mixture comprised: the cell lysate; 10 to 20 μl of the suspension comprising the magnetic particles at a concentration in the range of approximately 5-20 mg/ml; 10 to 20 μl of polyhydroxy polysaccharides, such as dextran, cellulose, and/or soluble starch at a concentration in the range of approximately 1 to 10 mg/ml; approximately 10 to 20 μl of anionic detergents, such as N-lauroyl sarcosine, sodium deoxycholate, CTAB, N-dodecyl β-D-maltoside, nonanoyl-N-methylglucamide, Triton® X-100, and/or sodium dodecyl sulfate; and approximately 150 to 300 μl of a polar compound such as isopropanol, ethanol, and/or PEG.

The DNA bound to the magnetic particles was physically separated from the binding mixture by the use of a magnetic field. The DNA bound to the magnetic particles was then washed with a wash solution. The DNA bound to the magnetic particles was physically separated from the wash mixture by use of a magnetic field. The wash step was repeated one to two times. The PCR inhibitors and other macromolecules entrapped in the DNA bound to the magnetic particles were removed in this step.

The DNA was then released from the magnetic particles by suspending the DNA bound to the magnetic particles in approximately 10 to 100 μl of aqueous solution, such as DNA-free water; or buffer comprising Tris-HCl and the chelating agent. The release mixture was incubated at a temperature in the range of approximately 50 to 75° C. Released genomic DNA was then physically separated from the magnetic particles by use of a magnetic field. The genomic DNA preparation thus obtained was stored at 4° C. for short-term storage, or at −20° C. for long-term storage. The DNA was quantified using standard methods well-known to those of skill in the art such as, for example, quantification of human DNA using the Quantifiler® Human DNA Quantification Kit. Results thus obtained, typical for human genomic DNA, are presented in Table 3.

TABLE 3

| Sample | Yield of DNA, ng |
| --- | --- |
| 2 μl liquid blood | 145 |
| 1 μl liquid semen | 650 |
| 20 μl liquid saliva | 165 |

Example 5

Genomic DNA was isolated as described in Example 4, wherein the biological fluids were 2 μl of blood, 20 μl of saliva and 1 μl of semen, and the fluids were stained on fabric such as cotton cloth, polyester cloth or denim. Results thus obtained for fluids stained on cotton, typical for human genomic DNA, are presented in Table 4.

TABLE 4

| Sample | Yield of DNA, ng |
| --- | --- |
| 2 μl blood on cotton | 80 |
| 1 μl semen on cotton | 550 |
| 20 μl saliva on cotton | 145 |

Example 6

Figure 2:
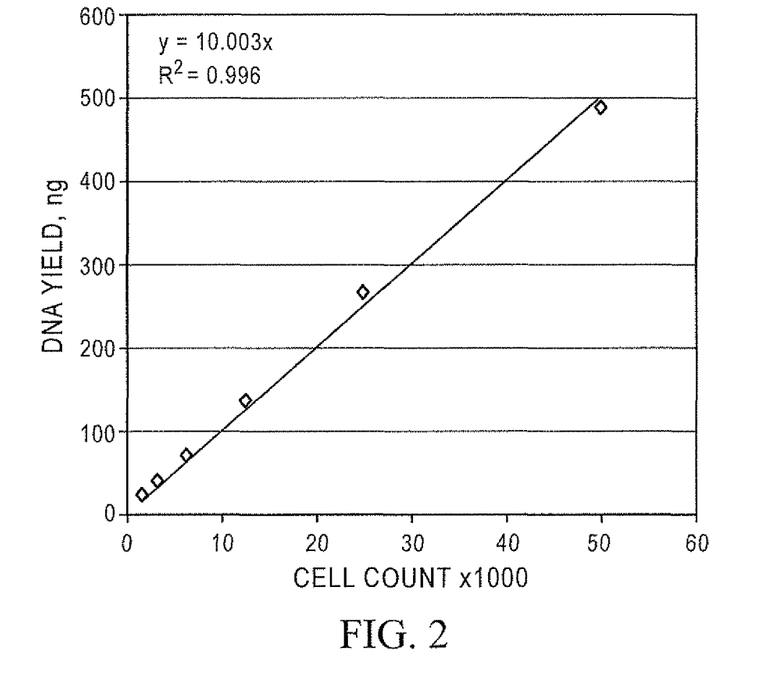
FIG. 2 demonstrates DNA yield from DNA isolation and purification as described in Example 6, wherein genomic DNA was isolated from cultured Raji cells at cell counts varying from 1562 to 50000, according to the methods described in Example 4.

Genomic DNA was isolated from cultured Raji cells at cell counts ranging from 1562 to 50000 cells, as described in Example 4. Results thus obtained, typical for human genomic DNA, are presented in FIG. 2 and Table 5.

TABLE 5

| Raji Cells, cell count | DNA yield, ng |
|---|---|
| 50000 | 488 |
| 25000 | 266 |
| 12500 | 136 |
| 6250 | 69.7 |
| 3125 | 37.3 |
| 1562 | 21 |

Example 7

Figure 3:
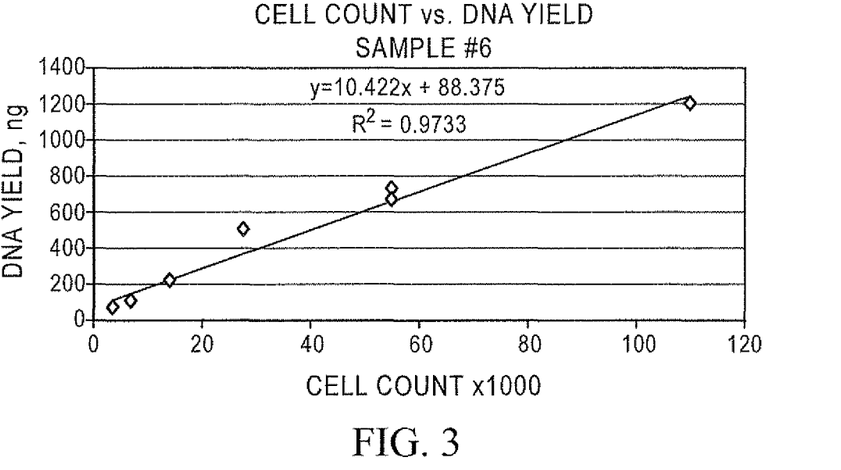
FIG. 3 demonstrates DNA yield from DNA isolation and purification as described in Example 7, wherein genomic DNA was isolated from cultured K562 cells at cell counts varying from 3500 to 110000, according to the methods as described in the Example 4.

Genomic DNA was isolated from cultured K562 cells at cell counts ranging from approximately 3500 to 110000 cells, as described in Example 4. Results thus obtained, typical for human genomic DNA, are presented in FIG. 3 and Table 6.

TABLE 6

| K562 Cells, cell count | DNA yield, ng |
|---|---|
| 110000 | 1190 |
| 55000 | 700 |
| 27500 | 500 |
| 13750 | 217 |
| 6875 | 114 |
| 3438 | 65 |

Example 8

Genomic DNA was isolated from biological fluids and stains of biological fluids on different substrates, such as cloth, FTA paper, a swab and denim, as described in Example 4, wherein the lysis of biological material was performed by suspending the biological material in a lysis solution. The lysis solution was incubated at a temperature in the range of 50 to 60° C. for a period of 40 minutes to 2 hours, and DNA was obtained and quantified by methods as outlined in Example 4.

Example 9

Genomic DNA was isolated as described in Example 4, wherein approximately 2 to 10 μl of the biological fluid blood was spotted on cotton, and was enriched with 1 to 5 μl of PCR inhibitors comprising hematin to a final concentration ranging from approximately 0.1 to 2 mM, humic acid to a final concentration ranging from approximately to 5 mg/ml, indigo to a final concentration ranging from 5 to 20 mM, and urban dust extract to a final concentration ranging from approximately 2 to 12 mg/ml. The PCR inhibitors were effectively removed during the extraction and isolation of the genomic DNA by these methods, as evidenced by measuring the $C_t$ value of the internal PCR control (IPC) using the Quantifiler® Human DNA Quantification Kit. Results thus obtained are presented in Table 7.

TABLE 7

| Sample | IPC $C_t$ |
|---|---|
| 2 μl blood dried on cotton | 27.58 |
| 2 μl blood dried on cotton in presence of inhibitors mix | 27.60 |
| Extraction Blank | 27.77 |

Example 10

Genomic DNA was isolated as described in the Example 4, wherein the biological samples comprising stains of biological fluids underwent environmental insults by exposure to the environment for a period of 1 to 7 days. DNA was isolated and quantified as per the methods of Example 4.

Example 11

Genomic DNA was isolated as described in Example 4, wherein the biological samples were of varying nature, comprising buccal swabs on the materials cotton, rayon, and nylon; blood, saliva and semen stains on materials like cotton cloth, denim, polyester cloth, FTA paper, filter paper; cigarette buts, swab of finger prints; mixtures of body fluids like epithelial cells and semen; swabs of body fluids on different surfaces.

Example 12

Genomic DNA was isolated from biological samples, as described in Example 11, and were processed for quantification of human DNA using the Quantifiler® Human DNA Quantification Kit. The results for the quantity of human DNA and the $C_t$ of the IPC, which measures the presence of PCR inhibitors from some typical substrates containing biological materials, are presented in Table 8. A positive difference greater than 1 in the IPC $C_t$ value for a sample DNA preparation relative to the IPC $C_t$ value of the negative template control (NTC) indicates the presence of PCR inhibitors.

TABLE 8

| Sample | DNA Yield, ng | IPC $C_t$ |
|---|---|---|
| Blood 2 μl | 62 ± 13 | 27.6 |
| Blood Stain 2 μl on denim | 76 ± 15 | 27.9 |
| Blood Stain 2 μl on rayon | 39.5 ± 8 | 27.7 |
| Blood Stain 2 μl on nylon | 39 ± 10 | 27.6 |
| Saliva 5 μl | 158 ± 30 | 27.6 |
| Saliva stain 5 μl on cotton | 143 ± 25 | 27.7 |
| Semen 2 μl | 1250 ± 150 | 27.6 |
| Semen stain 2 μl on cotton | 1340 ± 130 | 27.7 |
| Cigarette butt | 154 ± 40 | 27.8 |
| Chewing Gum | 21 ± 8 | 27.9 |
| Extraction Blank | 0 | 27.6 |
| NTC | | 27.6 |

Example 13

Figure 4A:
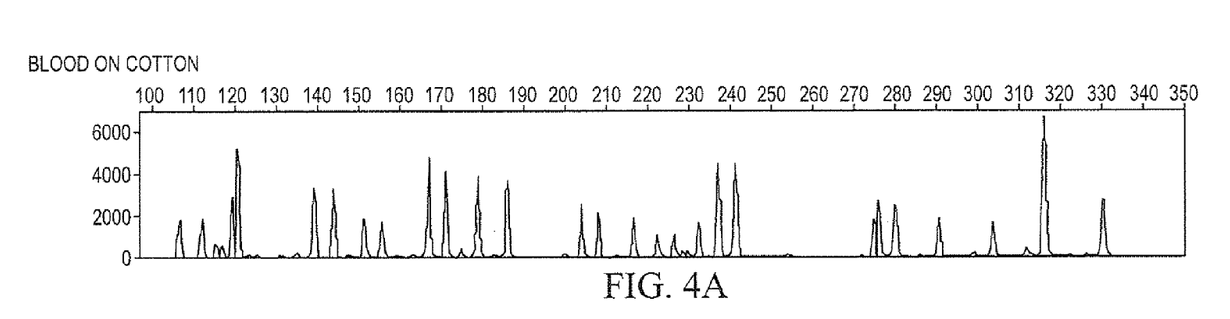
Figure 4B:
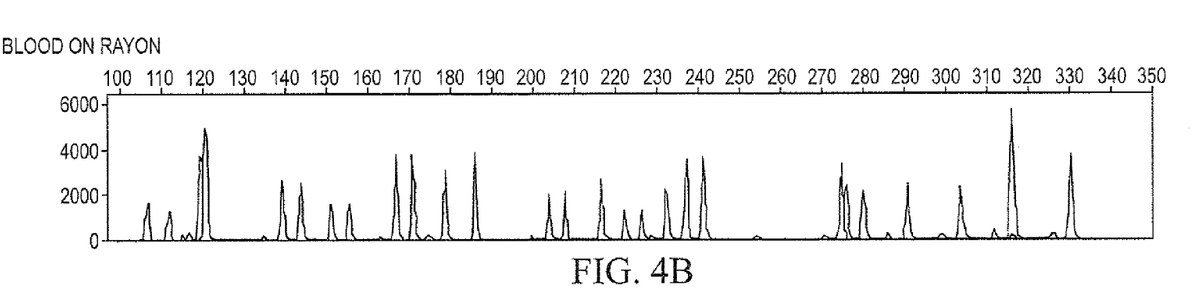
Figure 4C:
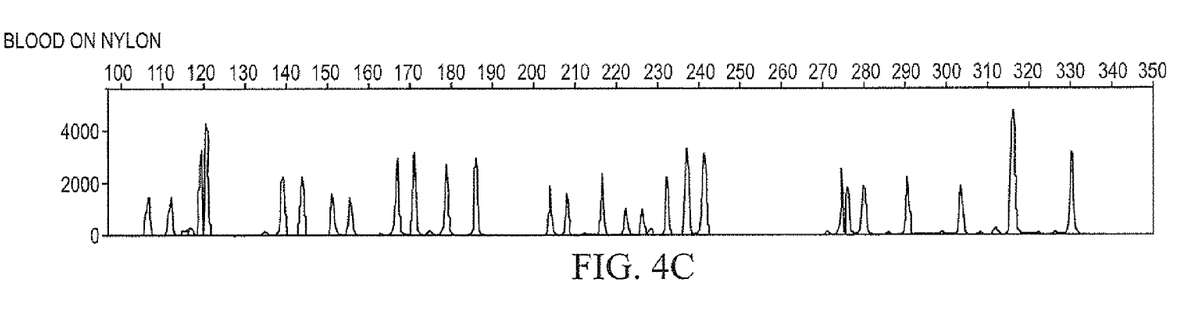
Figure 4D:
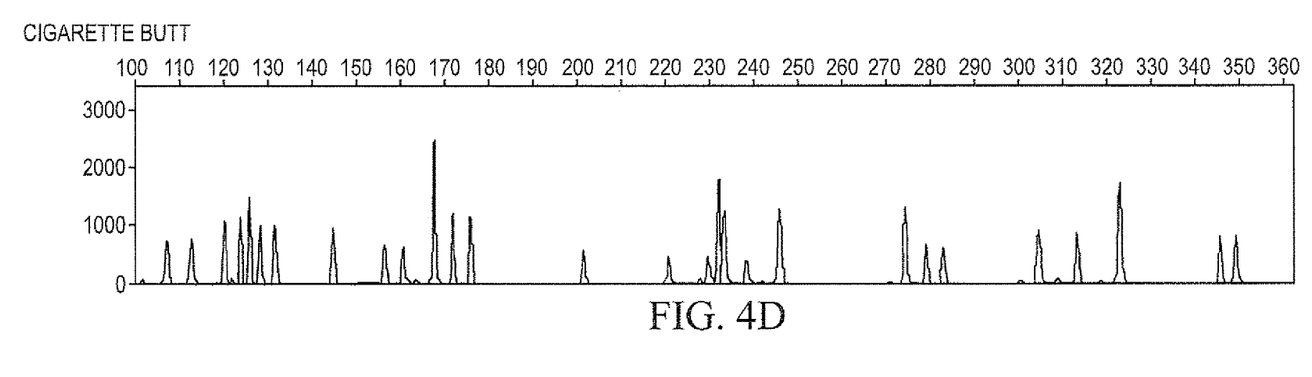
Figure 4E:
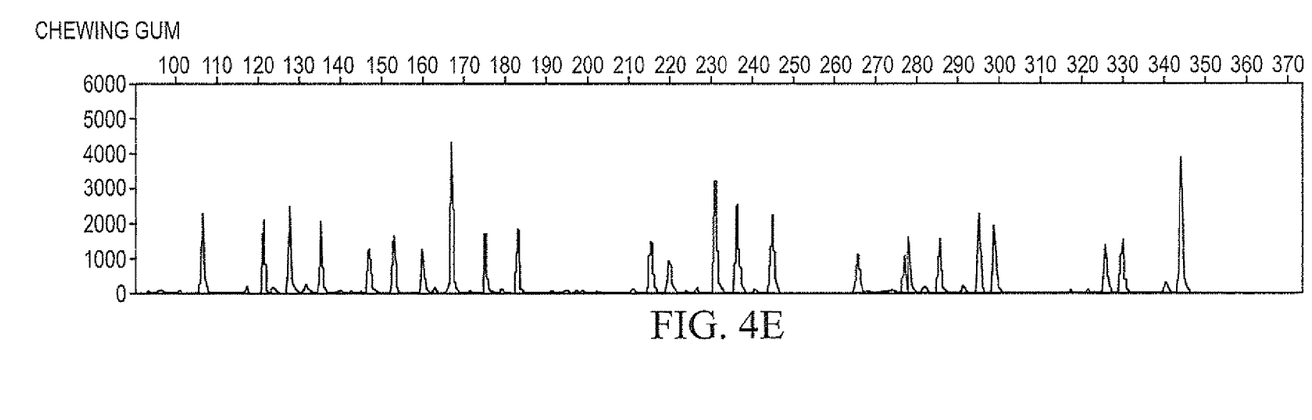

Genomic DNA was isolated from biological samples as described in Example 11, and were processed for genotyping using an AmpFISTR® kit, such as Identifiler®. The genotype profiles thus obtained from some typical substrates containing biological materials are presented in FIG. 4.

Example 14

Genomic DNA was isolated from biological samples as described in Examples 1 to 12, and was processed using the reagents as described therein in the form of a kit.

What is claimed is:

1. A composition comprising:
   a non-covalent complex comprising a nucleic acid, a polymer comprising dextran, and magnetically attractable particles comprising dextran encased magnetite nanoparticles, and
   a detergent, comprising N-lauroyl sarcosine or lauroyl sarcosinate.

2. The composition of claim 1, wherein the dextran is in the range of 1-5 mg/ml.

3. The composition of claim 1, wherein the dextran has a molecular weight of 5,000,000 to 40,000,000.

4. The composition of claim 1, wherein the lauroyl sarconsinate is in the range of about 5-15%.

5. The composition of claim 1, wherein the dextran encased particles are in the range of about 2-10 mg/ml.

* * * * *